(12) United States Patent
Joshi (10) Patent No.: US 11,684,622 B2
(45) Date of Patent: Jun. 27, 2023

(54) DEUTERATED RUC-4

(71) Applicant: CeleCor Therapeutics, Inc., San Diego, CA (US)

(72) Inventor: Yatindra Joshi, North Wales, PA (US)

(73) Assignee: CeleCor Therapeutics, Inc., Del Mar, CA (US)

( * ) Notice: Subject to any disclaimer, the term of this patent is extended or adjusted under 35 U.S.C. 154(b) by 25 days.

(21) Appl. No.: 17/253,427

(22) PCT Filed: Jun. 18, 2019

(86) PCT No.: PCT/US2019/037713
§ 371 (c)(1),
(2) Date: Dec. 17, 2020

(87) PCT Pub. No.: WO2019/246085
PCT Pub. Date: Dec. 26, 2019

(65) Prior Publication Data
US 2021/0361658 A1    Nov. 25, 2021

Related U.S. Application Data

(60) Provisional application No. 62/687,150, filed on Jun. 19, 2018.

(51) Int. Cl.
*A61K 31/519* (2006.01)
*A61K 31/122* (2006.01)
(Continued)

(52) U.S. Cl.
CPC .......... *A61K 31/519* (2013.01); *A61K 31/122* (2013.01); *A61K 31/37* (2013.01);
(Continued)

(58) Field of Classification Search
CPC .. A61K 31/122; A61K 31/37; A61K 31/4365; A61K 31/4465; A61K 31/519; A61K 31/616; A61K 31/702; A61K 31/727; A61K 38/12; A61K 38/482; A61K 39/3955; A61K 45/06; C07B 2200/05; C07D 513/04
See application file for complete search history.

(56) References Cited

U.S. PATENT DOCUMENTS

| 4,265,898 A | 5/1981 | Horstmann et al. |
| 6,221,335 B1 * | 4/2001 | Foster .................. C07B 59/002 |
| | | 424/1.81 |

(Continued)

FOREIGN PATENT DOCUMENTS

| CN | 104936598 A | 9/2015 |
| WO | WO 2009/024615 A1 | 2/2009 |
| WO | WO 2019/246085 A1 | 12/2019 |

OTHER PUBLICATIONS

Wolen, Journal of Clinical Pharmacology 1986; 26: 419-424, (Year: 1986).*

(Continued)

*Primary Examiner* — Savitha M Rao
(74) *Attorney, Agent, or Firm* — Wolf, Greenfield & Sacks, P.C.

(57) ABSTRACT

Provided herein are deuterated RUC-4 compounds, and related compositions and therapeutic methods.

20 Claims, 6 Drawing Sheets

| Compound Name | d$_8$-RUC-4 2HCl |
|---|---|
| Lot Number | 18-0203-005-25-25 |
| Molecular weight | 467.40 |
| UPLC, RRT = 1.00 | 93.28 area% |
| TGA | 7.61 % weight loss |
| LCMS | [M + H]$^+$ 395.3 |

Overall purity = UPLC area% - TGA weight loss
Overall purity = 93.28 - 7.61 = 85.67 %

(51) Int. Cl.
| | |
|---|---|
| *A61K 31/37* | (2006.01) |
| *A61K 31/4365* | (2006.01) |
| *A61K 31/4465* | (2006.01) |
| *A61K 31/616* | (2006.01) |
| *A61K 31/702* | (2006.01) |
| *A61K 31/727* | (2006.01) |
| *A61K 38/12* | (2006.01) |
| *A61K 38/48* | (2006.01) |
| *A61K 39/395* | (2006.01) |
| *C07D 513/04* | (2006.01) |

(52) U.S. Cl.
CPC ...... *A61K 31/4365* (2013.01); *A61K 31/4465* (2013.01); *A61K 31/616* (2013.01); *A61K 31/702* (2013.01); *A61K 31/727* (2013.01); *A61K 38/12* (2013.01); *A61K 38/482* (2013.01); *A61K 39/3955* (2013.01); *C07D 513/04* (2013.01); *C07B 2200/05* (2013.01)

(56) References Cited

U.S. PATENT DOCUMENTS

| | | | | |
|---|---|---|---|---|
| 6,603,008 | B1* | 8/2003 | Ando | A61P 25/00 546/271.4 |
| 7,517,990 | B2* | 4/2009 | Ito | C07D 233/56 546/184 |
| 9,303,044 | B2 | 4/2016 | Coller et al. | |
| 9,532,989 | B2* | 1/2017 | Coller | C07D 487/04 |
| 2007/0082929 | A1* | 4/2007 | Gant | A61P 1/04 546/273.7 |
| 2007/0197695 | A1* | 8/2007 | Potyen | C08K 5/55 524/110 |
| 2015/0050325 | A1 | 2/2015 | Coller et al. | |

OTHER PUBLICATIONS

Extended European Search Report for EP 19823013.8, dated Feb. 25, 2022.
Baba et al., Studies on drug metabolism by use of isotopes. 23. Metabolic study of 1-butyryl-4-cinnamylpiperazine in the rat during development of tolerance by using two kinds of deuterium-labeled forms. J Med Chem. Jun. 1978;21(6):525-9. doi: 10.1021/jm00204a005.
PCT/US2022/016564, May 4, 2022, International Search Report and Written Opinion.
PCT/US2022/016571, May 3, 2022, International Search Report and Written Opinion.
International Search Report and Written Opinion for Application No. PCT/US2022/016564, dated May 4, 2022.
International Search Report and Written Opinion for Application No. PCT/US2022/016571, dated May 3, 2022.
Declaration under 37 C.F.R. § 1.32 of Vinita Uttamsingh, dated Feb. 1, 2012. 3 pages. Filed in U.S. Appl. No. 12/102,164, filed Apr. 14, 2008.
Harbeson et al., Chapter 24: Deuterium in Drug Discovery and Development. Annual Reports in Medicinal Chemistry. Concert Pharmaceuticals, Inc. Lexington, MA. 2011;46:403-417.
Jiang et al., A novel class of ion displacement ligands as antagonists of the αIIbβ3 receptor that limit conformational reorganization of the receptor. Bioorg Med Chem Lett. Feb. 15, 2014;24(4):1148-53. doi: 10.1016/j.bmcl.2013.12.122. Epub Jan. 8, 2014.
Kereiakes et al., First Human Use of RUC-4: A Nonactivating Second-Generation Small-Molecule Platelet Glycoprotein IIb/IIIa (Integrin αIIbβ3) Inhibitor Designed for Subcutaneous Point-of-Care Treatment of ST-Segment-Elevation Myocardial Infarction. J Am Heart Assoc. Sep. 2020;9(17):e016552. doi: 10.1161/JAHA.120.016552. Epub Aug. 26, 2020.
Li et al., RUC-4: a novel αIIbβ3 antagonist for prehospital therapy of myocardial infarction. Arterioscler Thromb Vase Biol. Oct. 2014;34(10):2321-9. doi: 10.1161/ATVBAHA.114.303724. Epub Aug. 21, 2014.
No Author Listed, Pubchem SID: 384568713. Deposit Date: Jun. 21, 2019. 7 pages.
Savonitto et al., Antithrombotic therapy before, during and after emergency angioplasty for ST elevation myocardial infarction. Eur Heart J Acute Cardiovasc Care. Mar. 2017;6(2):173-190. doi: 10.1177/2048872615590148. Epub Sep. 22, 2016.
Shao et al., Derivatives of tramadol for increased duration of effect. Bioorg Med Chem Lett. Feb. 2006;16(3):691-4. doi: 10.1016/j.bmcl.2005.10.024. Epub Oct. 27, 2005.
Strickley, Solubilizing excipients in oral and injectable formulations. Pharm Res. Feb. 2004;21(2):201-30. doi: 10.1023/b:pham.0000016235.32639.23.
Xu et al., High-sensitive cardiac troponin T. J Geriatr Cardiol. Mar. 2013;10(1):102-9. doi: 10.3969/j.issn.1671-5411.2013.01.015.
Liu, Deuterated Drugs Progress. Chemical Engineering Design Communications. Apr. 2016; 42(4): 199 and 238.
PCT/US2019/037713, Aug. 23, 2019, International Search Report and Written Opinion.
PCT/US2019/037713, Dec. 30, 2020, International Preliminary Report on Patentabilty.
International Search Report and Written Opinion for PCT/US2019/037713, dated Aug. 23, 2019.
International Preliminary Report on Patentabilty for PCT/US2019/037713, dated Dec. 30, 2020.

* cited by examiner

| | |
|---|---|
| Compound Name | $d_8$-RUC-4 2HCl |
| Lot Number | 18-0203-005-25-25 |
| Molecular weight | 467.40 |
| UPLC, RRT = 1.00 | 93.28 area% |
| TGA | 7.61 % weight loss |
| LCMS | $[M + H]^+$ 395.3 |

Overall purity = UPLC area% - TGA weight loss
Overall purity = 93.28 − 7.61 = 85.67 %

FIG. 1

Chromatogram and Results

Injection Details

| | | | |
|---|---|---|---|
| Injection Name: | 18-0203-005-25-25; RUC4-D8 HCl salt (07-03-18) | Run Time (min): | 29.00 |
| Vial Number: | GA2 | Injection Volume: | 10.00 |
| Injection Type: | Unknown | Channel: | UV_VIS_1 |
| Calibration Level: | | Wavelength: | 238.0 |
| Instrument Method: | RUC-4 SB Rev18 | Bandwidth: | n.a. |
| Processing Method: | Processing Method_05-24-18 | Dilution Factor: | 1.0000 |
| Injection Date/Time: | 03/Jul/18 09:21 | Sample Weight: | 1.0000 |

Integration Results

| No. | Peak Name | Retention Time min | Area mAU*min | Height mAU | Relative Area % | Relative Height % | Amount |
|---|---|---|---|---|---|---|---|
| 1 | | 7.616 | 0.124 | 1.795 | 0.24 | 0.29 | n.a. |
| 2 | | 7.974 | 0.234 | 3.416 | 0.45 | 0.55 | n.a. |
| 3 | | 8.590 | 1.105 | 15.296 | 2.14 | 2.46 | n.a. |
| 4 | | 9.024 | 48.279 | 569.348 | 93.28 | 91.58 | n.a. |
| 5 | | 9.941 | 0.505 | 6.238 | 0.97 | 1.00 | n.a. |
| 6 | | 10.541 | 0.136 | 2.095 | 0.26 | 0.34 | n.a. |
| 7 | | 10.715 | 0.491 | 7.164 | 0.95 | 1.15 | n.a. |
| n.a. | Azo-Imp | n.a. | n.a. | n.a. | n.a. | n.a. | n.a. |
| n.a. | From blank | n.a. | n.a. | n.a. | n.a. | n.a. | n.a. |
| 8 | | 14.824 | 0.224 | 3.397 | 0.43 | 0.55 | n.a. |
| 9 | | 16.424 | 0.658 | 12.948 | 1.27 | 2.08 | n.a. |
| Total: | | | 51.756 | 621.698 | 100.00 | 100.00 | |

FIG. 2

18-0203-005-25-25
RUC-4-08 HCl salt
exp3 Proton

SAMPLE
date         Jul 2 2018
solvent              d2o
file/home/pharnd/~
vnmrsys/data/auto_
2018.03.30_01/s_20~
180702_01/data/d2o~
_02.fid
ACQUISITION
sw           6399.0
at            2.049
np           26218
fb            4000
bs              32
ss               2
dl             000
nt              04
ct              04
TRANSMITTER
tn              H1
sfrq       999.950
tof         399.9
tpwr           53
pw          4.550
DECOUPLER
dn             C13
dof             0
dm            nnn
dmm            C
dpwr           40
dmf          18500

SPECIAL
temp         24.0
gain      not used
spin            20
hst          0.008
sw50        9.100
alfa         6.600
FLAGS
fl               n
fn               n
dp               y
hs              nn
PROCESSING
fn           65536
DISPLAY
sp           -6.3
wp         4155.8
ff1        2651.2
ffT        1915.7
rp          106.7
lp          -51.1
PLOT
wc            250
sc              0
vs             77
th              5
al  cdc  ph

DEUTERATED RUC-4

CROSS REFERENCE TO RELATED APPLICATIONS

This present application is a National Stage Application of PCT/US2019/037713, filed on Jun. 18, 2019, which claims priority of U.S. Provisional Application No. 62/687,150, filed Jun. 19, 2018, which applications are incorporated herein by reference.

BACKGROUND

Many small molecule pharmaceuticals suffer from poor absorption, distribution, metabolism and/or excretion (ADME) properties that limit their use in certain indications or otherwise prevent their use. Unfavorable ADME properties are also a common reason for the failure of drug candidates in clinical trials. In some cases, formulation technologies and prodrug strategies can be employed to improve ADME properties. However, these approaches often fail to address the underlying ADME problems. One such problem, rapid metabolism, causes a number of drugs that otherwise would be highly effective in treating a disease to be cleared too rapidly from the body. One solution to rapid drug clearance is frequent or high dosing to attain a sufficiently high plasma level of drug. However, this approach may introduce a number of potential treatment problems such as poor patient compliance with the dosing regimen, side effects that become more acute with higher doses, and increased cost of treatment. A rapidly metabolized drug may also expose patients to undesirable toxic or reactive metabolites.

Another unfavorable ADME outcome that affects many small molecule pharmaceuticals is the formation of toxic or biologically reactive metabolites. As a result of exposure to such metabolites, patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

A potentially attractive strategy for improving a drug's ADME properties is deuteration (i.e., replacing one or more hydrogen atoms with deuterium). Deuterium is a safe, stable, non-radioactive isotope of hydrogen. Compared to hydrogen, deuterium forms stronger bonds with carbon. In some cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M. I. et al., J. Pharm. Sci., 1975, 64:367-91; Foster, A. B., Adv. Drug. Res. 1985, 14:1-40; Kushner, D. J. et al., Can. J. Physiol. Pharmacol. 1999, 79-88; Fisher, M. B. et al., Curr. Opin. Drug Discov. Devel., 2006, 9:101-09). The results have been variable and unpredictable. For some compounds, deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism.

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

RUC-4, also known as 2-amino-N-(5-(5-oxo-7-(piperazin-1-yl)-5H-[1,3,4]thiadiazolo[3,2-a]pyrimidin-2-yl)pyridin-3-yl)acetamide, is an inhibitor of the platelet integrin αIIbβ3 (a receptor on the surface of human platelets) that is used for the treatment and prophylaxis of diseases or disorders associated with abnormalities in platelet adhesion and aggregation and arterial thrombosis. Methods of making and using RUC-4 are disclosed in U.S. Pat. No. 9,303,044, which is incorporated herein by reference in its entirety. Diseases and disorders associated with abnormalities in platelet adhesion and aggregation and arterial thrombosis include, for example, stroke, coronary artery disease/myocardial infarction, cerebrovascular disease, peripheral vascular disease, stable and unstable angina, transient ischemic attacks, placental insufficiency, unwanted thromboses subsequent to surgical procedures (e.g., aortocoronary bypass surgery, angioplasty and stent placement, and heart valve replacement), thrombotic disorders resulting from atrial fibrillation, or disorders involving inflammation, particularly allergic inflammation (e.g., in asthma) and inflammation at the sites of atherosclerotic damage.

Despite the beneficial properties of RUC-4, improvements in the ADME properties of RUC-4, and further advances in the treatment of disorders that may be treated by an inhibitor of αIIbβ3 are desirable.

SUMMARY

In one aspect, provided herein is a compound of Formula (I):

or a pharmaceutically acceptable salt thereof, wherein:
each of $R_a$, $R_b$, $R_c$, $R_d$, $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ independently are hydrogen or deuterium;
provided that at least one of $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ is deuterium.

In certain embodiments, the compound of Formula (I) is of Formulae (II), (III), (III-1), (IV), (IV-1), (V), (V-1), (VI), and (VI-1), each of which are described below, and pharmaceutically acceptable salts thereof.

In another aspect, provided herein is a method for the treatment or prevention of a thrombotic disorder, comprising administering to a subject in need thereof an effective amount of a compound of Formula (I), or a pharmaceutically acceptable salt thereof.

In another aspect, provided herein is a method for inhibiting or reducing platelet aggregation and adhesion, comprising administering to a subject in need thereof an effective amount of a compound of Formula (I), or a pharmaceutically acceptable salt thereof.

DETAILED DESCRIPTION

Definitions

The term "isotopologue" refers to a molecule that differs from another molecule of the same chemical structure only in its isotopic composition.

It will be understood that some variation of natural isotopic abundance occurs in a synthetic compound depending on the origin of materials (e.g., starting materials, reagents, and solvents) used in the synthesis. Thus, a preparation of non-isotopically enriched compound "RUC-4" (2-amino-N-(5-(5-oxo-7-(piperazin-1-yl)-5H-[1,3,4]thiadiazolo[3,2-a]pyrimidin-2-yl)pyridin-3-yl)acetamide) will inevitably contain small amounts of isotopologues (comprising, e.g., $^2$H and $^{14}$C). In such a non-isotopically enriched compound, however, the abundance of naturally abundant stable hydrogen and carbon isotopes is small and immaterial as compared to the abundance of stable isotopic substituents (e.g., deuterium) in compounds of the invention. See, for instance, Wada, E et al., Seikagaku, 1994, 66:15; Gannes, L. Z. et al., Comp Biochem. Physiol. Mol. Integr. Physiol, 1998, 119:725.

In the compounds of the invention, any atom not specifically designated as a particular isotope is meant to represent any stable isotope of that atom. Unless otherwise stated, when a position is designated as "H" or "hydrogen", the position is understood to have hydrogen at its natural abundance isotopic composition. Also, unless otherwise stated, when a position is specifically designated as "D" or "deuterium", the position is understood to have deuterium at an abundance that is at least 3000 times greater than the natural abundance of deuterium, which is 0.015% (i.e., at least 45% incorporation of deuterium).

As used herein, the term "compound," refers to a collection of molecules having an identical chemical structure, except that there may be isotopic variation among the constituent atoms of the molecules. Thus, it will be clear to those of skill in the art that a compound represented by a particular chemical structure, containing indicated deuterium atoms, will also contain lesser amounts of isotopologues having hydrogen atoms at one or more of the designated deuterium positions in that structure. The relative amount of such isotopologues in a compound of the invention will depend upon a number of factors, including the isotopic purity of deuterated reagents used to make the compound, and the efficiency of incorporation of deuterium in the synthesis steps used to prepare the compound. However, as set forth above, the relative amount of such isotopologues in total will be less than 55% of the compound. In certain embodiments, the relative amount of such isotopologues in total will be less than 50%, less than 45%, less than 40%, less than 35%, less than 30%, less than 25%, less than 20%, less than 15%, less than 10%, less than 5%, less than 2.5%, less than 1%, or less than 0.5% of the compound.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In certain particular embodiments, a pharmaceutically acceptable salt of a compound described herein is a hydrochloride salt, e.g., a mono-hydrochloride salt, or a dihydrochloride salt.

Compounds of the Invention

In various aspects, deuterated compounds of Formulae (I), (II), (III), (IV), (V), (VI) and pharmaceutically acceptable salts thereof, are provided. These compounds and salts, as well as hydrates, solvates, polymorphs, and solid forms thereof are collectively referred to as compounds of the invention.

Formula (I)

In one aspect, provided herein is a compound of Formula (I):

(I)

or a pharmaceutically acceptable salt thereof, wherein:
each of $R_a$, $R_b$, $R_c$, $R_d$, $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ independently are hydrogen or deuterium;
provided that at least one of $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ is deuterium.

In certain embodiments, one or more of $R_a$, $R_b$, $R_c$, $R_d$ is deuterium. In certain embodiments, each of $R_a$, $R_b$, $R_c$, $R_d$ is hydrogen.

In certain embodiments, at least two, at least three, at least four, at least five, at least six, at least seven, at least eight, at least nine, at least ten, at least eleven, at least twelve, at least thirteen, or at least fourteen of $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ are deuterium. In certain embodiments, 1, 2, 3, 4, 5, 6, 7, 8, 9, 10, 11, 12, 13, 14, or 15 of $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ are deuterium.

Formula (II)

In certain embodiments, the compound of Formula (I) is of Formula (II):

(II)

or a pharmaceutically acceptable salt thereof.

Formula (III)

In certain embodiments, the compound of Formula (I) is of Formula (III):

(III)

or a pharmaceutically acceptable salt thereof.

In certain embodiments, at least one of $R_3$, $R_4$, and $R_6$ is deuterium. In certain embodiments, at least two of $R_3$, $R_4$, and $R_6$ are deuterium. In certain embodiments, all three of $R_3$, $R_4$, and $R_6$ are deuterium.

In certain embodiments, at least one of $R_3$, $R_4$, and $R_6$ is hydrogen. In certain embodiments, at least two of $R_3$, $R_4$, and $R_6$ are hydrogen. In certain embodiments, all three of $R_3$, $R_4$, and $R_6$ are hydrogen.

In certain embodiments, $R_7$ is deuterium. In certain embodiments, $R_7$ is hydrogen.

In certain embodiments, at least one of $R_8$, $R_9$, $R_{10}$, $R_{11}$, $R_{12}$, $R_{13}$, $R_{14}$, and $R_{15}$ is deuterium. In certain embodiments, at least two of $R_8$, $R_9$, $R_{10}$, $R_{11}$, $R_{12}$, $R_{13}$, $R_{14}$, and $R_{15}$ are deuterium. In certain embodiments, at least three of $R_8$, $R_9$, $R_{10}$, $R_{11}$, $R_{12}$, $R_{13}$, $R_{14}$, and $R_{15}$ are deuterium. In certain embodiments, at least four of $R_8$, $R_9$, $R_{10}$, $R_{11}$, $R_{12}$, $R_{13}$, $R_{14}$, and $R_{15}$ are deuterium. In certain embodiments, at least five of $R_8$, $R_9$, $R_{10}$, $R_{11}$, $R_{12}$, $R_{13}$, $R_{14}$, and $R_{15}$ are deuterium. In certain embodiments, at least six of $R_8$, $R_9$, $R_{10}$, $R_{11}$, $R_{12}$, $R_{13}$, $R_{14}$, and $R_{15}$ are deuterium. In certain embodiments, at least seven of $R_8$, $R_9$, $R_{10}$, $R_{11}$, $R_{12}$, $R_{13}$, $R_{14}$, and $R_{15}$ are deuterium. In certain embodiments, each of $R_8$, $R_9$, $R_{10}$, $R_{11}$, $R_{12}$, $R_{13}$, $R_{14}$, and $R_{15}$ is deuterium.

In certain embodiments, at least one of $R_8$, $R_9$, $R_{10}$, $R_{11}$, $R_{12}$, $R_{13}$, $R_{14}$, and $R_{15}$ is hydrogen. In certain embodiments, at least two of $R_8$, $R_9$, $R_{10}$, $R_{11}$, $R_{12}$, $R_{13}$, $R_{14}$, and $R_{15}$ are hydrogen. In certain embodiments, at least three of $R_8$, $R_9$, $R_{10}$, $R_{11}$, $R_{12}$, $R_{13}$, $R_{14}$, and $R_{15}$ are hydrogen. In certain embodiments, at least four of $R_8$, $R_9$, $R_{10}$, $R_{11}$, $R_{12}$, $R_{13}$, $R_{14}$, and $R_{15}$ are hydrogen. In certain embodiments, at least five of $R_8$, $R_9$, $R_{10}$, $R_{11}$, $R_{12}$, $R_{13}$, $R_{14}$, and $R_{15}$ are hydrogen. In certain embodiments, at least six of $R_8$, $R_9$, $R_{10}$, $R_{11}$, $R_{12}$, $R_{13}$, $R_{14}$, and $R_{15}$ are hydrogen. In certain embodiments, at least seven of $R_8$, $R_9$, $R_{10}$, $R_{11}$, $R_{12}$, $R_{13}$, $R_{14}$, and $R_{15}$ are hydrogen. In certain embodiments, each of $R_8$, $R_9$, $R_{10}$, $R_{11}$, $R_{12}$, $R_{13}$, $R_{14}$, and $R_{15}$ is hydrogen.

In certain particular embodiments, the compound of Formula (III) is of Formula (III-1):

(III-1)

or a pharmaceutically acceptable salt thereof.
Formula (IV)
In certain particular embodiments, the compound of Formula (I) is of Formula (IV):

(IV)

or a pharmaceutically acceptable salt thereof.
In certain embodiments, at least one of $R_1$ and $R_2$ is deuterium. In certain embodiments, each of $R_1$ and $R_2$ is deuterium.
In certain embodiments, at least one of $R_1$ and $R_2$ is hydrogen. In certain embodiments, each of $R_1$ and $R_2$ is hydrogen.
In certain embodiments, $R_7$ is deuterium. In certain embodiments, $R_7$ is hydrogen.

In certain embodiments, at least one of $R_8$, $R_9$, $R_{10}$, $R_{11}$, $R_{12}$, $R_{13}$, $R_{14}$, and $R_{15}$ is deuterium. In certain embodiments, at least two of $R_8$, $R_9$, $R_{10}$, $R_{11}$, $R_{12}$, $R_{13}$, $R_{14}$, and $R_{15}$ are deuterium. In certain embodiments, at least three of $R_8$, $R_9$, $R_{10}$, $R_{11}$, $R_{12}$, $R_{13}$, $R_{14}$, and $R_{15}$ are deuterium. In certain embodiments, at least four of $R_8$, $R_9$, $R_{10}$, $R_{11}$, $R_{12}$, $R_{13}$, $R_{14}$, and $R_{15}$ are deuterium. In certain embodiments, at least five of $R_8$, $R_9$, $R_{10}$, $R_{11}$, $R_{12}$, $R_{13}$, $R_{14}$, and $R_{15}$ are deuterium. In certain embodiments, at least six of $R_8$, $R_9$, $R_{10}$, $R_{11}$, $R_{12}$, $R_{13}$, $R_{14}$, and $R_{15}$ are deuterium. In certain embodiments, at least seven of $R_8$, $R_9$, $R_{10}$, $R_{11}$, $R_{12}$, $R_{13}$, $R_{14}$, and $R_{15}$ are deuterium. In certain embodiments, each of $R_8$, $R_9$, $R_{10}$, $R_{11}$, $R_{12}$, $R_{13}$, $R_{14}$, and $R_{15}$ are deuterium.

In certain embodiments, at least one of $R_8$, $R_9$, $R_{10}$, $R_{11}$, $R_{12}$, $R_{13}$, $R_{14}$, and $R_{15}$ is hydrogen. In certain embodiments, at least two of $R_8$, $R_9$, $R_{10}$, $R_{11}$, $R_{12}$, $R_{13}$, $R_{14}$, and $R_{15}$ are hydrogen. In certain embodiments, at least three of $R_8$, $R_9$, $R_{10}$, $R_{11}$, $R_{12}$, $R_{13}$, $R_{14}$, and $R_{15}$ are hydrogen. In certain embodiments, at least four of $R_8$, $R_9$, $R_{10}$, $R_{11}$, $R_{12}$, $R_{13}$, $R_{14}$, and $R_{15}$ are hydrogen. In certain embodiments, at least five of $R_8$, $R_9$, $R_{10}$, $R_{11}$, $R_{12}$, $R_{13}$, $R_{14}$, and $R_{15}$ are hydrogen. In certain embodiments, at least six of $R_8$, $R_9$, $R_{10}$, $R_{11}$, $R_{12}$, $R_{13}$, $R_{14}$, and $R_{15}$ are hydrogen. In certain embodiments, at least seven of $R_8$, $R_9$, $R_{10}$, $R_{11}$, $R_{12}$, $R_{13}$, $R_{14}$, and $R_{15}$ are hydrogen. In certain embodiments, each of $R_8$, $R_9$, $R_{10}$, $R_{11}$, $R_{12}$, $R_{13}$, $R_{14}$, and $R_{15}$ are hydrogen.

In certain particular embodiments, the compound of Formula (IV) is of Formula (IV-1):

(IV-1)

or a pharmaceutically acceptable salt thereof.
Formula (V)
In certain particular embodiments, the compound of Formula (I) is of Formula (V):

(V)

or a pharmaceutically acceptable salt thereof.
In certain embodiments, at least one of $R_1$ and $R_2$ is deuterium. In certain embodiments, each of $R_1$ and $R_2$ is deuterium.
In certain embodiments, at least one of $R_1$ and $R_2$ is hydrogen. In certain embodiments, each of $R_1$ and $R_2$ is hydrogen.

In certain embodiments, at least one of $R_3$, $R_4$, and $R_6$ is deuterium. In certain embodiments, at least two of $R_3$, $R_4$, and $R_6$ are deuterium. In certain embodiments, all three of $R_3$, $R_4$, and $R_6$ are deuterium.

In certain embodiments, at least one of $R_3$, $R_4$, and $R_6$ are hydrogen. In certain embodiments, at least two of $R_3$, $R_4$, and $R_6$ are hydrogen. In certain embodiments, all three of $R_3$, $R_4$, and $R_6$ are hydrogen.

In certain embodiments, at least one of $R_8$, $R_9$, $R_{10}$, $R_{11}$, $R_{12}$, $R_{13}$, $R_{14}$, and $R_{15}$ is deuterium. In certain embodiments, at least two of $R_8$, $R_9$, $R_{10}$, $R_{11}$, $R_{12}$, $R_{13}$, $R_{14}$, and $R_{15}$ are deuterium. In certain embodiments, at least three of $R_8$, $R_9$, $R_{10}$, $R_{11}$, $R_{12}$, $R_{13}$, $R_{14}$, and $R_{15}$ are deuterium. In certain embodiments, at least four of $R_8$, $R_9$, $R_{10}$, $R_{11}$, $R_{12}$, $R_{13}$, $R_{14}$, and $R_{15}$ are deuterium. In certain embodiments, at least five of $R_8$, $R_9$, $R_{10}$, $R_{11}$, $R_{12}$, $R_{13}$, $R_{14}$, and $R_{15}$ are deuterium. In certain embodiments, at least six of $R_8$, $R_9$, $R_{10}$, $R_{11}$, $R_{12}$, $R_{13}$, $R_{14}$, and $R_{15}$ are deuterium. In certain embodiments, at least seven of $R_8$, $R_9$, $R_{10}$, $R_{11}$, $R_{12}$, $R_{13}$, $R_{14}$, and $R_{15}$ are deuterium. In certain embodiments, each of $R_8$, $R_9$, $R_{10}$, $R_{11}$, $R_{12}$, $R_{13}$, $R_{14}$, and $R_{15}$ are deuterium.

In certain embodiments, at least one of $R_8$, $R_9$, $R_{10}$, $R_{11}$, $R_{12}$, $R_{13}$, $R_{14}$, and $R_{15}$ is hydrogen. In certain embodiments, at least two of $R_8$, $R_9$, $R_{10}$, $R_{11}$, $R_{12}$, $R_{13}$, $R_{14}$, and $R_{15}$ are hydrogen. In certain embodiments, at least three of $R_8$, $R_9$, $R_{10}$, $R_{11}$, $R_{12}$, $R_{13}$, $R_{14}$, and $R_{15}$ are hydrogen. In certain embodiments, at least four of $R_8$, $R_9$, $R_{10}$, $R_{11}$, $R_{12}$, $R_{13}$, $R_{14}$, and $R_{15}$ are hydrogen. In certain embodiments, at least five of $R_8$, $R_9$, $R_{10}$, $R_{11}$, $R_{12}$, $R_{13}$, $R_{14}$, and $R_{15}$ are hydrogen. In certain embodiments, at least six of $R_8$, $R_9$, $R_{10}$, $R_{11}$, $R_{12}$, $R_{13}$, $R_{14}$, and $R_{15}$ are hydrogen. In certain embodiments, at least seven of $R_8$, $R_9$, $R_{10}$, $R_{11}$, $R_{12}$, $R_{13}$, $R_{14}$, and $R_{15}$ are hydrogen. In certain embodiments, each of $R_8$, $R_9$, $R_{10}$, $R_{11}$, $R_{12}$, $R_{13}$, $R_{14}$, and $R_{15}$ are hydrogen.

In certain particular embodiments, the compound of Formula (V) is of Formula (V-1):

(V-1)

or a pharmaceutically acceptable salt thereof.
Formula (VI)
In certain particular embodiments, the compound of Formula (I) is of Formula (VI):

(VI)

or a pharmaceutically acceptable salt thereof.

In certain embodiments, at least one of $R_1$ and $R_2$ is deuterium. In certain embodiments, each of $R_1$ and $R_2$ is deuterium.

In certain embodiments, at least one of $R_1$ and $R_2$ is hydrogen. In certain embodiments, each of $R_1$ and $R_2$ is hydrogen.

In certain embodiments, at least one of $R_3$, $R_4$, and $R_6$ is deuterium. In certain embodiments, at least two of $R_3$, $R_4$, and $R_6$ are deuterium. In certain embodiments, all three of $R_3$, $R_4$, and $R_6$ are deuterium.

In certain embodiments, at least one of $R_3$, $R_4$, and $R_6$ is hydrogen. In certain embodiments, at least two of $R_3$, $R_4$, and $R_6$ are hydrogen. In certain embodiments, all three of $R_3$, $R_4$, and $R_6$ are hydrogen.

In certain embodiments, $R_7$ is deuterium. In certain embodiments, $R_7$ is hydrogen.

In certain particular embodiments, the compound of Formula (VI) is of Formula (VI-1):

(VI-1)

or a pharmaceutically acceptable salt thereof.

In certain embodiments of the compounds of the invention, any atom not designated as deuterium is present at its natural isotopic abundance. In certain embodiments of the compounds of the invention, the deuterium incorporation at each atom designated as deuterium is at least 45%, e.g., at least 50%, at least 60%, at least 70%, or at least 80%. In certain embodiments, the deuterium incorporation at each atom designated as deuterium is at least 90%, e.g., at least 91%, at least 92%, at least 93%, at least 94%, at least 95%, at least 96%, at least 97%, at least 98%, or at least 99%. In certain embodiments, the compounds of the invention exhibit improved or advantageous ADME properties as compared to the non-isotopically enriched compound "RUC-4" (2-amino-N-(5-(5-oxo-7-(piperazin-1-yl)-5H-[1,3,4]thiadiazolo[3,2-a]pyrimidin-2-yl)pyridin-3-yl)acetamide), having the following structural formula:

In certain embodiments, the improved pharmacokinetic property (ADME) is improved metabolic stability.

In another aspect, provided herein is a pharmaceutical composition comprising a compound of the invention and a pharmaceutically acceptable carrier. The compound maybe be in free or pharmaceutically acceptable salt form, and is in combination or association with the pharmaceutically acceptable diluent or carrier. The pharmaceutical compositions of the invention as hereinbefore described are useful, e.g., for preventing or inhibiting platelet adhesion and/or aggregation in treating thrombotic a disorder in a subject in need thereof. In yet another embodiment, the invention provides the pharmaceutical compositions of the invention as hereinbefore described useful for inhibiting or reducing platelet aggregation and/or adhesion.

In another aspect, provided herein is a pharmaceutical composition comprising a compound of the invention and a pharmaceutically acceptable carrier or diluent, for use as a pharmaceutical e.g., (in the manufacture of a medicament) for the treatment or prophylaxis of a thrombotic disorder, e.g., according to any the presently disclosed methods. The compound may be in free or pharmaceutically acceptable salt form as hereinbefore described.

Therapeutic Methods and Uses

In another aspect, provided herein is a method for the treatment or prevention of a thrombotic disorder, comprising administering to a subject in need thereof an effective amount of a compound of the invention. The compounds of the invention may be administered orally or parenterally, including intravenous, intramuscular, intraperitoneal, subcutaneous, transdermal, airway (aerosol), rectal, vaginal and topical (including buccal and sublingual) administration. The compounds useful in the invention may generally be provided in the form of tablets or capsules, as a powder or granules, or as an aqueous and/or non-aqueous solutions, creams, ointments, gels, or suspensions. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Dosages of the compounds of the invention will vary depending upon the condition to be treated or prevented and on the identity of the inhibitor being used. Estimates of effective dosages and in vivo half-lives for the individual compounds encompassed by the invention can be made on the basis of in vivo testing using an animal model, such as the mouse model described herein or an adaptation of such method to larger mammals. In certain embodiments, appropriate dosage may range from 0.01 mg to 5000 mg. In certain embodiments, appropriate dosage may range from 0.01 mg to 100 mg. In certain embodiments, an appropriate dosage may be 0.01-30 mg/Kg, e.g., about 12 mg/Kg, or about 26.5 mg/Kg. In other embodiments, an appropriate dosage may range from 0.01-1.5 mg/Kg, e.g., about 0.1 mg/Kg, about 0.5 mg/Kg, about 1 mg/Kg, or about 1.5 mg/Kg. The administering physician can adjust the amount and timing of drug administration on the basis of results observed using standard measures of platelet activity known in the art or described herein.

The term "subject" may include human or non-human (e.g., an animal). In certain embodiments, the subject is human. In certain embodiments, the subject is suffering from a thrombotic disorder. Thrombotic disorders are disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation. In certain embodiments, the subject is at risk of developing a thrombotic disorder. A "subject at risk of developing a thrombotic disorder" or "subject in need thereof" includes subjects who have a history of vascular intervention (e.g. angioplasty, stent placement, aortocoronary bypass or insertion of prosthetic heart valves), cardiovascular abnormality (e.g. atrial fibrillation) or a family history of vascular diseases (e.g., coronary artery disease (CAD), systemic hypertension, diabetes mellitus, hyperlipidemia, bicuspid aortic valve, hypertrophic cardiomyopathy or mitral valve prolapse).

In certain embodiments, the thrombotic disorder is selected from stroke, myocardial infarction, unstable angina, abrupt closure following angioplasty or stent placement, thrombosis induced by peripheral vascular surgery, peripheral vascular disease and thrombotic disorders resulting from atrial fibrillation or inflammation.

In certain embodiments, the method results in reduction of platelet aggregation and/or adhesion in the subject. In certain embodiments, the method results in reduction of both platelet aggregation and platelet adhesion in the subject.

In certain embodiments, the method further comprises administering to the subject the compound of this invention, with or without formulation with other excipients, along with an effective amount of at least one therapeutic agent selected from the group consisting of anti-coagulant agents, antiplatelet agents, and fibrinolytic agents. These therapeutic agents may be heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, ticagrelor, abciximab, eptifibatide and tirofiban. One or more of these therapeutic agents may be administered sequentially (e.g., before or after) or simultaneously with the compound of the invention.

In another aspect, provided herein is a method for inhibiting or reducing platelet aggregation and adhesion, comprising administering to a subject in need thereof an effective amount of a compound of the invention.

In certain embodiments, the subject is human.

In certain embodiments, the method results in reduction of platelet aggregation and/or adhesion in the subject. In certain embodiments, the method results in reduction of both platelet aggregation and platelet adhesion in the subject.

In certain embodiments, the reduction of platelet aggregation and/or adhesion treats or prevents a thrombotic disorder, e.g. stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

EXAMPLES

Synthesis of Compounds of the Present Invention

The compounds described herein and their pharmaceutically acceptable salts may be made using the methods as described and exemplified herein and by methods similar thereto and by methods known in the chemical art. In addition, the compounds of the invention may be made by using similar methods as those described in PCT/US11/44267. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, reaction may require to be run at elevated temperature, for a longer or shorter period of time or in the presence of an acid or base. It is understood by one skilled in the art of organic synthesis that functionality present on various portions of the molecule must be compatible with the reagents and reactions proposed. If not commercially available, starting materials for these processes may be made by procedures, which are selected from the chemical art using techniques similar or analogous to the synthesis of known compounds. Significances of the substituents are as set forth in the formulae hereinbefore defined unless otherwise specified. All references cited herein are hereby incorporated in their entirety by reference.

General Synthetic Procedures.

The synthesis methods described above and/or the following general procedures are used to synthesize compounds having different but analogous structures.

Example 1—Synthesis of (1) 2-amino-N-(5-(5-oxo-7-(piperazin-1-yl)-5H-[1,3,4]thiadiazolo[3,2-a]pyrimidin-2-yl)pyridin-3-yl)acetamide-2,2-$d_2$ 5-nitronicotinic acid (500 mg, 2.97 mmol) is mixed with thionyl chloride (15 ml, 206 mmol) and the mixture is heated at 80° C. for 3.5 h. After the removal of thionyl chloride, the residue is dissolved in pyridine (2 ml) and thiosemicarbazide (271 mg, 2.97 mmol) is added. The mixture is stirred overnight at room temperature. The mixture is poured into ice and the precipitate is filtered and washed with EtOAc to give the desired product as a gray solid (110 mg, 15%).

PPA (2 ml) is preheated to 100° C. and the 2-(5-nitronicotinoyl) hydrazinecarbothioamide (110 mg, 0.46 mmol) is added portionwise. The mixture is heated at this temperature for 1 h. After cooling to room temperature, the mixture is slowly poured into ice and the pH is adjusted to 9.0 with the addition of ammonium hydroxide solution (37 wt % in water). The solid precipitates out and is filtered and washed with EtOAc (3×5 ml). The EtOAc is combined, washed with brine and dried over sodium sulfate. After the removal of most EtOAc, the solid is filtered which is combined with the solid obtained in the first filtration to give the desired product, 5-(5-nitropyridin-3-yl)-1,3,4-thiadiazol-2-amine, as a light yellow solid (100 mg, 98%).

To a solution 5-(5-nitropyridin-3-yl)-1,3,4-thiadiazol-2-amine (80 mg g, 0.36 mmol) in $CH_3CN$ (3.4 ml) is added methyl 3-chloro-3-oxopropanoate (0.054 ml, 0.50 mmol). The mixture is microwaved at 100° C. for 12 min. After cooling to room temperature, $POCl_3$ (1.34 ml, 14.34 mmol) and Hunig's base (0.063 ml, 0.36 mmol) are added and the mixture is microwaved at 150° C. for 30 min. After cooling to room temperature, excess $POCl_3$ and $CH_3CN$ are 15 removed in vacuo and the residue is dissolved in DCM and poured into ice. The DCM solution is washed with saturated aqueous $NaHCO_3$ solution and the organic layer is separated (due to the formation of polyphosphoric acid, filtration of the organic and aqueous layers through Celite is needed to remove the sticky material). The organic layer is washed with brine and dried over $Na_2SO_4$. After the removal of organic solvent in vacuo, the crude residue is purified by Biotage column chromatography (EtOAc/DCM: 1/100 to 1/20 gradient) to give the desired product, 7-chloro-2-(2-chloropyridin-4-yl)-5H-[1,3,4]thiadiazolo[3,2-a]pyrimidin-5-one (30 mg, 27%) as a yellow solid.

To a mixture of 7-chloro-2-(2-chloropyridin-4-yl)-5H-[1,3,4]thiadiazolo[3,2-a]pyrimidin-5-one (30 mg, 0.097 mmol) and tert-butyl piperazine-1-carboxylate (22 mg, 0.12 mmol) in $CH_3CN$ (2 ml) is added Hunig's (0.024 ml, 0.140 mmol) and the mixture is microwaved at 100° C. for 1 h. After cooling to room temperature, solid starts to precipitate out. The solid is filtered, washed with EtOAc and collected. The filtrate is concentrated in vacuo and the crude residue is purified by Biotage column chromatography (MeOH/DCM: 1/100 to 1/10 gradient) to give another portion of product. The total amount of desired product, tert-butyl 4-(2-(5-nitropyridin-3-yl)-5-40 oxo-5H-[1,3,4]thiadiazolo[3,2-a]pyrimidin-7-yl)piperazine-1-carboxylate, is 40 mg (yield: 90%).

To a solution of tert-butyl 4-(2-(5-nitropyridin-3-yl)-5-oxo-5H-[1,3,4]thiadiazolo[3,2-a]pyrimidin-7-yl)piperazine-1-carboxylate (40 mg, 0.087 mmol) in MeOH (3 ml) is added Raney-nickel in water slurry. Then hydrazine (0.027 ml, 0.87 mmol) is added dropwise. After the completion of addition, the mixture is stirred for another 5 min, then filtered through a pad of Celite to remove the catalyst. The filtrate is concentrated in vacuo and dried under vacuo to give the desired product, tert-butyl 4-(2-(5-aminopyridin-3-yl)-5-oxo-5H-[1,3,4]thiadiazolo[3,2-a]pyrimidin-7-yl)piperazine-1-carboxylate (20 mg, 54%).

To a solution of tert-butyl 4-(2-(5-aminopyridin-3-yl)-5-oxo-5H-[1,3,4]thiadiazolo[3,2-a]pyrimidin-7-yl)piperazine-1-carboxylate (20 mg, 0.047 mmol) in DMF (1 ml) is added Boc-Gly-OH-2,2-$d_2$ (0.093 mmol), HATU (35 mg, 0.093 mmol) and Hunig's base (0.024 mmol, 0.14 mmol) and the mixture is stirred at room temperature for 3 h. EtOAc (10 ml) is added and the solution is washed with $H_2O$ and brine. The organic layer is dried over $Na_2SO_4$. After removing EtOAc in vacuo, the residue is purified by Biotage column chromatography (MeOH/DCM: 1/100 to 1/10 gradient) to give the desired product, tert-butyl 4-(2-(5-(2-aminoacetamido-2,2-$d_2$)pyridin-3-yl)-5-oxo-5H-[1,3,4]thiadiazolo[3,2-a]pyrimidin-7-yl)piperazine-1-carboxylate.

To a solution of tert-butyl 4-(2-(5-(2-aminoacetamido-2,2-$d_2$)pyridin-3-yl)-5-oxo-5H-[1,3,4]thiadiazolo[3,2-a]pyrimidin-7-yl)piperazine-1-carboxylate (0.045 mmol) in DCM (2 ml) is added TFA (0.5 ml) and the mixture is stirred for 1 hours. After the removal of DCM in vacuo, the crude residue is directly purified by preparative HPLC to give the desired product, 2-amino-N-(5-(5-oxo-7-(piperazin-1-yl)-5H-[1,3,4]thiadiazolo[3,2-a]pyrimidin-2-yl)pyridin-3-yl)acetamide-2,2-$d_2$.

Example 2—Synthesis of (2) 2-amino-N-(5-(5-oxo-7-(piperazin-1-yl)-5H-[1,3,4]thiadiazolo[3,2-a]pyrimidin-2-yl)pyridin-3-yl-2,4,6-$d_3$)acetamide Compound (2) is prepared analogously to Compound (1), by substituting 5-nitronicotinic-2,4,6-$d_3$ acid for 5-nitronicotinic acid.

Example 3—Synthesis of (3) 2-amino-N-(3-(5-oxo-7-(piperazin-1-yl-2,2,3,3,5,5,6,6-$d_8$)-5H-[1,3,4]thiadiazolo[3,2-a]pyrimidin-2-yl)phenyl)acetamide Compound (3) is prepared analogously to Compound (1), by substituting tert-butyl piperazine-1-carboxylate-2,2,3,3,5,5,6,6-ds for tert-butyl piperazine-1-carboxylate.

Example 4—Synthesis of (3) 2-amino-N-(3-(5-oxo-7-(piperazin-1-yl-2,2,3,3,5,5,6,6-$d_8$)-5H-[1,3,4]thiadiazolo[3,2-a]pyrimidin-2-yl)phenyl)acetamide Scheme 2

Figure 1:
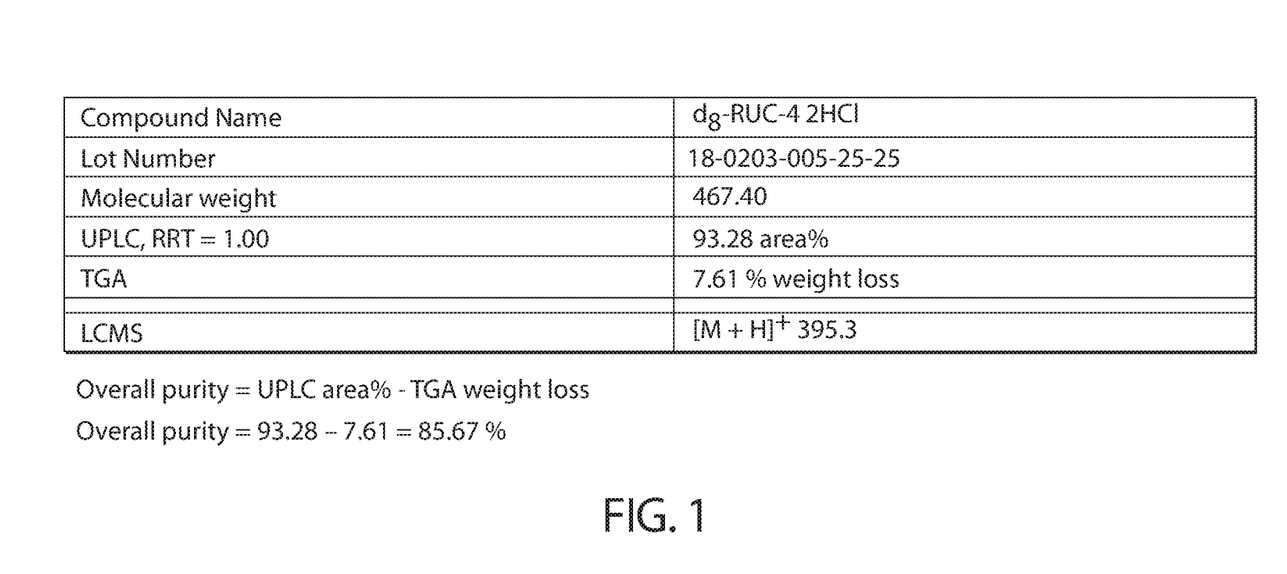
FIG. 1 summarizes the results of analytical testing of Compound 3.
Figure 2:
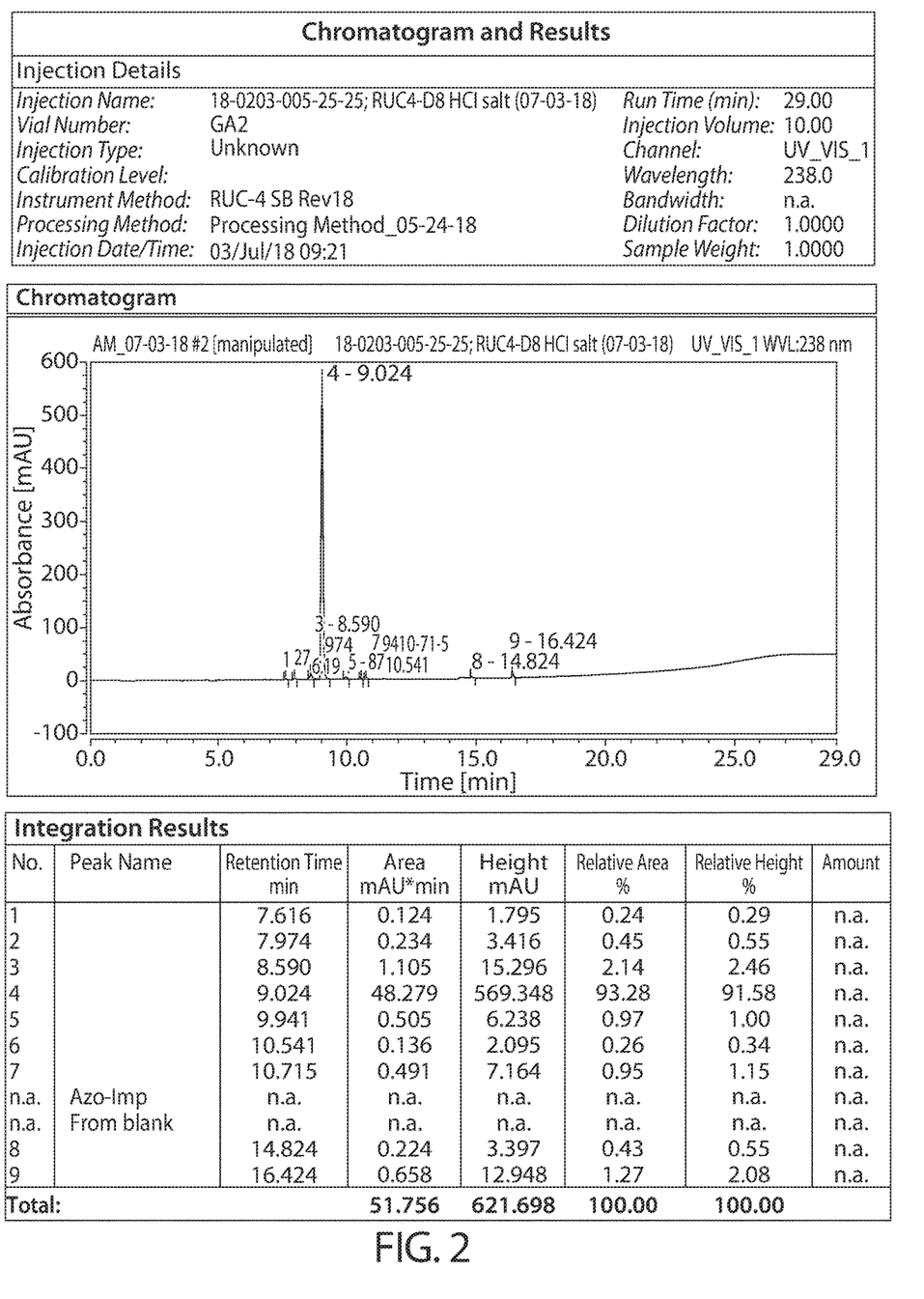
FIG. 2 shows an HPLC chromatogram of Compound 3.
Figure 3:
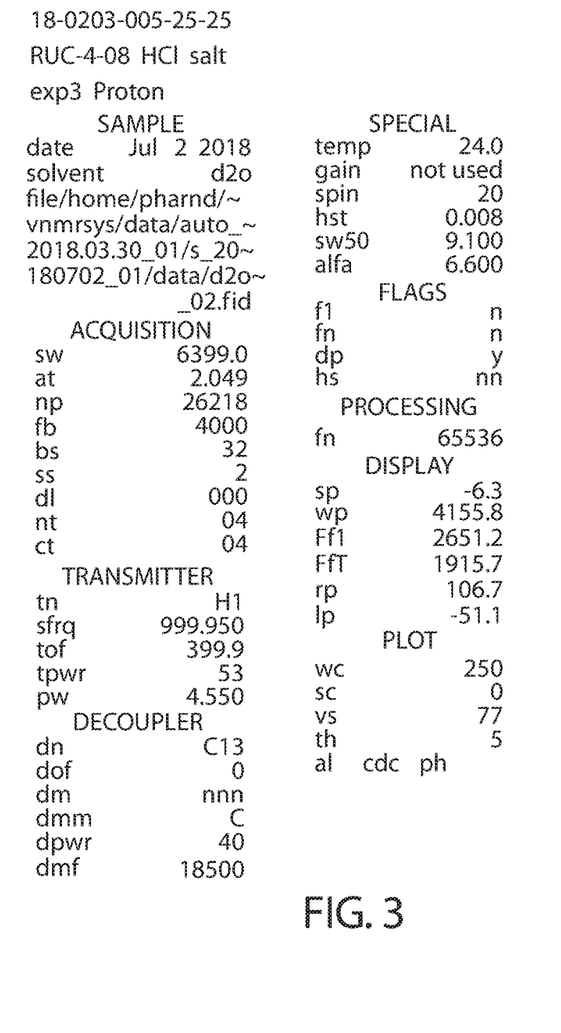
FIG. 3 shows an $^1$HNMR spectrum of Compound 3.
Figure 4:
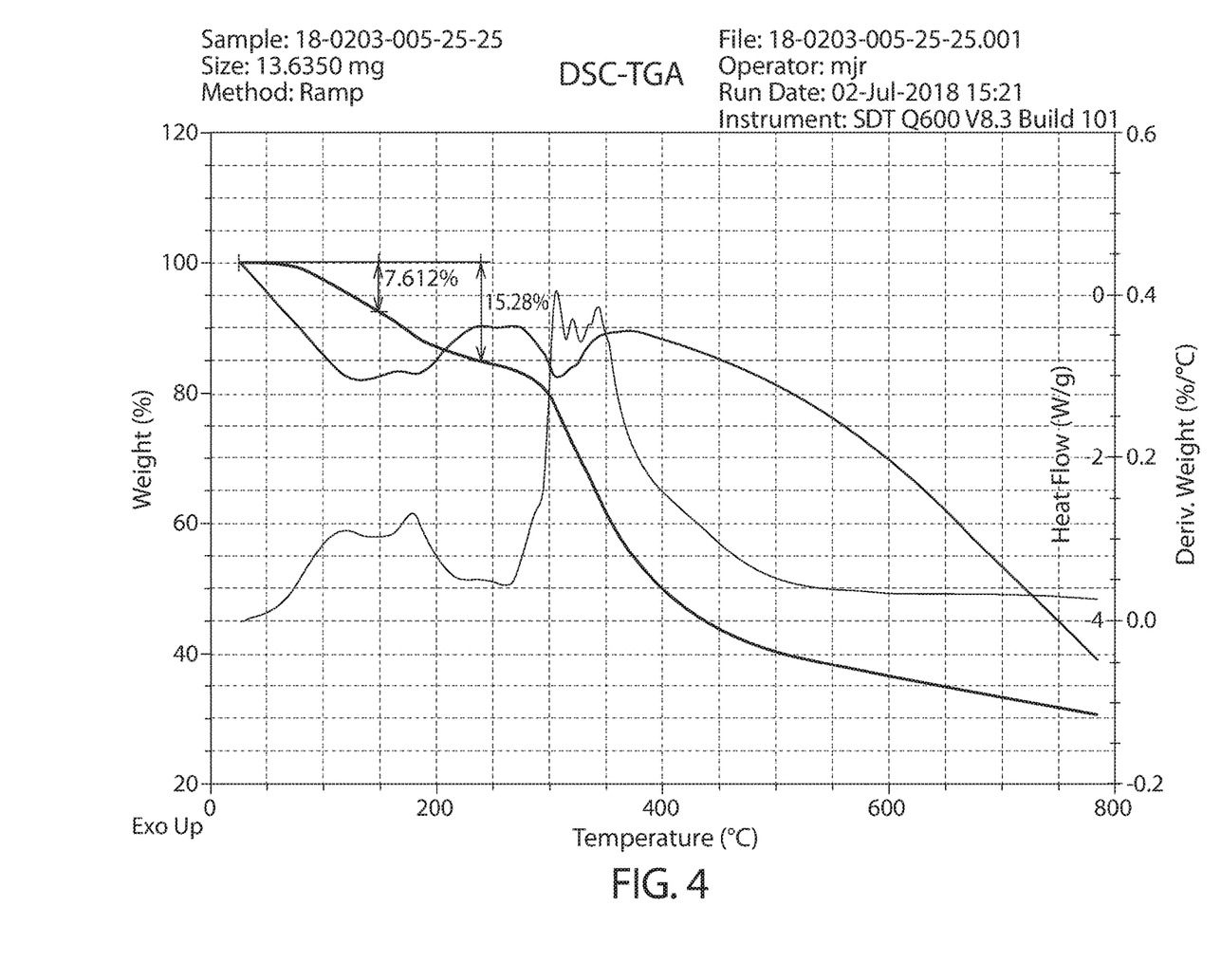
FIG. 4 shows results of DSC-TGA analysis of Compound 3.
Figure 5:
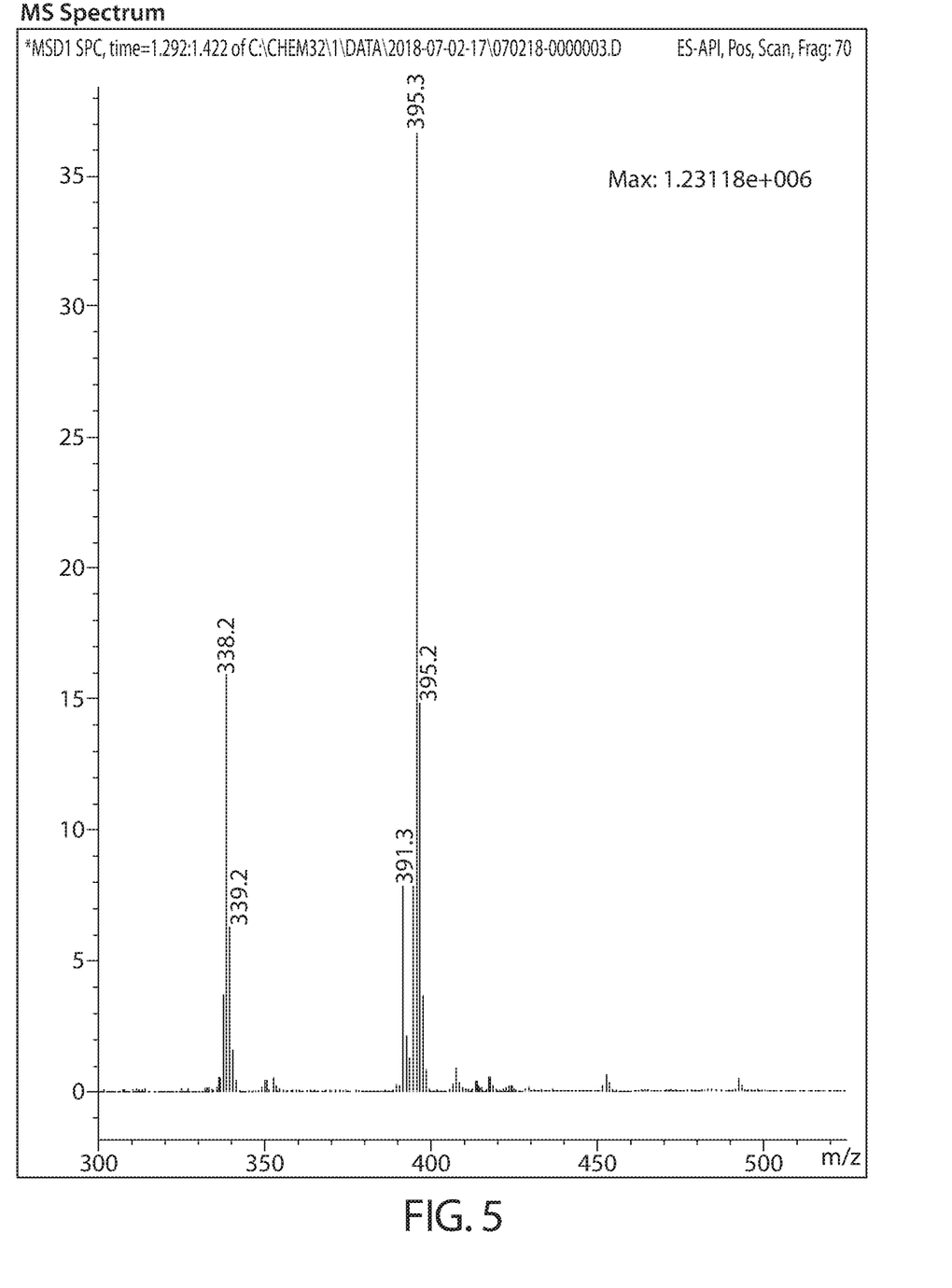
FIG. 5 shows the mass spectrum of Compound 3.

As shown in Scheme 2, an alternative synthesis of Compound (3) started with compound (8). Thus, compound (8) was coupled with commercially available ds-Boc-piperazine (9) using PyBop as the coupling reagent, diisopropylethyl amine (DIEA) as base and DMF as solvent to produce compound (10) in 17% yield. Compound (10) was reduced to compound (11) using iron and aqueous ammonium chloride in a solvent system of DCM and methanol (76% yield). Compound (11) was coupled with Boc-glycine (12) using T3P (n-propanephosphonic acid anhydride) as the coupling reagent, pyridine as base, and DMF as solvent to produce compound (13) in 53% yield. Compound (13) was Boc-deprotected using 4M HCl in dioxane with DCM as solvent to produce the dihydrochloride salt of Compound (3) in quantitative yield. Compound (3) was characterized by $^1$H NMR, LCMS, UPLC, and TGA.

General synthesis details: Unless otherwise noted, solvents and reagents were used without purification. Volatile solvents were removed under reduced pressure using a Buchi rotary evaporator. Thin layer chromatography (TLC) was performed on glass-backed pre-coated silica gel plates (0.25 mm thick with 60 F254) and were visualized using one or both of the following manners: UV light (254 nm) and/or staining with $I_2$ impregnated silica. Flash chromatography was performed using a Biotage Isolera One using pre-loaded Silicycle high performance (14-40 μM) columns. $^1$H nuclear magnetic resonance (NMR) spectra were obtained at 400 MHz as indicated as solutions in DMSO-$d_6$ or $D_2O$ with 0.05% v/v tetramethylsilane (TMS) unless indicated otherwise.

Detailed synthesis of compound (10): A 20 mL reaction vial, equipped with a magnetic stir bar, was charged with compound (8) (0.755, g, 2.3 mmol, 1.0 equiv) and DMF (11.5 mL). DIEA (1.4 mL, 8.1, mmol, 3.5 equiv) was added dropwise. The reaction became homogeneous. PyBop (1.80 g, 3.46 mmol, 1.5 equiv) was added portion-wise as a solid. Deuterated piperazine (9) (0.447 g, 2.3 mmol, 1.3 equiv) was added and the reaction mixture was stirred overnight at ambient temperature. A sample was removed for in-process analysis by LCMS, which showed some (8) remaining but no (9) remaining. MTBE (10 mL) was added to the reaction mixture and the resulting suspension was centrifuged. The supernatant was decanted and the solids were suspended in MTBE and centrifuged. This process was repeated twice more. The solids were dried overnight under high vacuum. The crude material was purified by silica gel column chromatography (heptanes/acetone, gradient, 10 to 60% acetone). Pure fractions were combined and concentrated to afford compound (10) (0.18 g, 0.39 mmol, 17% recovery).

Detailed synthesis of compound (11). A 40 mL reaction vial, equipped with a magnetic stir bar, was charged with iron powder (215 mg, 3.85 mmol, 10 equiv) and $NH_4Cl$ (206 mg, 3.85 mmol, 10 equiv). Water (5 mL) was added and the mixture was heated to 35° C. Compound (10) (180 mg, 0.385 mmol, 1.0 equiv) was dissolved in a mixture of MeOH/DCM (8 ml, 111, v/v). The solution of (10) was added to the reaction mixture over 15 min. Heating was stopped and the reaction mixture was stirred at ambient temperature overnight. A sample was removed for in-process analysis by LCMS, which showed complete conversion. The reaction mixture was vacuum filtered through Celite and the vial and Celite were washed with MeOH/DCM (10 mL, 111, v/v). The combined filtrate and wash were filtered through a 0.45 micron PTFE membrane. The filtrate was concentrated and the residue was azeotroped with toluene (3 15 mL). The residue was suspended in MeOH/DCM (20 mL, 1/1, v/v) and filtered through a 0.45 micron PTFE membrane (2×). The residue was dried (high vacuum pump, ambient temperature) overnight to give 11 (128 mg, 76% recovery).

Detailed synthesis of Compound (3). A 20 mL reaction vial, equipped with a magnetic stir bar, was charged with (13) (85 mg, 0.142 mmol, 1.0 equiv), and DCM (4 mL). Hydrochloric acid (4M solution in dioxane, 0.71 mL, 2.84 mmol, 20 equiv) was added and the mixture was stirred at ambient temperature for 1 h. A sample was removed for in-process analysis by TLC, which showed complete conversion. The reaction mixture was concentrated. The residue was suspended in DCM (5 mL) and concentrated (2×). The residue was triturated with MTBE (10 mL) and the supernatant was decanted. The solids were dried overnight (high vacuum pump, ambient temperature) overnight to give Compound (3) (68 mg, 103% recovery).

Example 5—Synthesis of (4) 2-amino-N-(3-(5-oxo-7-(piperazin-1-yl)-5H-[1,3,4]thiadiazolo[3,2-a]pyrimidin-2-yl-6-d)phenyl)acetamide Compound (4) is prepared analogously to Compound (1), by substituting methyl 3-chloro-3-oxopropanoate-2,2-d2 for methyl 3-chloro-3-oxopropanoate.

Example 6—Evaluation of Metabolic Stability

Microsomal Assay:
Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.
Determination of Metabolic Stability:
7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compounds of the invention and the positive control, 7-ethoxycoumarin (1 µM). Testing is done in triplicate.
Data Analysis:
The in vitro $t_{1/2}$s for test compounds are calculated from the slopes of the linear regression of % parent remaining (ln) vs incubation time relationship.
in vitro $t_{1/2} = 0.693/k$

$k = -$[slope of linear regression of % parent remaining (ln) vs incubation time]

Data analysis is performed using Microsoft Excel Software.
Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

The invention claimed is:
1. A compound of Formula (I):

or a pharmaceutically acceptable salt thereof, wherein:
each of $R_a$, $R_b$, $R_c$, $R_d$, $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ independently are hydrogen or deuterium;
provided that at least one of $R_1$, $R_2$, $R_3$, $R_4$, $R_6$, $R_7$, $R_8$, $R_9$, $R_{10}$, $R_{11}$, $R_{12}$, $R_{13}$, $R_{14}$, and $R_{15}$ is deuterium.
2. The compound of claim 1, of Formula (II):

of Formula (III):

of Formula (IV):

of Formula (V):

or of Formula (VI):

or a pharmaceutically acceptable salt thereof.

3. The compound of claim 1, wherein at least one of $R_3$, $R_4$, and $R_6$ is deuterium.

4. The compound of claim 1, wherein at least one of $R_3$, $R_4$, and $R_6$ is hydrogen.

5. The compound of claim 1, wherein $R_7$ is deuterium.

6. The compound of claim 1, wherein at least one of $R_8$, $R_9$, $R_{10}$, $R_{11}$, $R_{12}$, $R_{13}$, $R_{14}$, and $R_{15}$ is deuterium.

7. The compound of claim 2 of Formula (III-1):

of Formula (IV-1):

of Formula (V-1):

or of Formula (VI-1):

or a pharmaceutically acceptable salt thereof.

8. The compound of claim 1, wherein any atom not designated as deuterium is present at its natural isotopic abundance, and wherein the deuterium incorporation at each atom designated as deuterium is at least 90%.

9. The compound of claim 1, wherein the compound exhibits improved pharmacokinetic and/or pharmacodynamic properties as compared to 2-amino-N-(5-(5-oxo-7-(piperazin-1-yl)-5H-[1,3,4]thiadiazolo[3,2-a]pyrimidin-2-yl)pyridin-3-yl)acetamide, or a pharmaceutically acceptable salt thereof.

10. The compound of claim 9, wherein the pharmacokinetic property is metabolic stability.

11. A pharmaceutical composition comprising a compound of claim 1, or a pharmaceutically acceptable salt thereof, and a pharmaceutically acceptable carrier.

12. A method for the treatment or prevention of a thrombotic disorder, comprising administering to a subject in need thereof an effective amount of a compound of claim 1, or a pharmaceutically acceptable salt thereof.

13. The method of claim 12, wherein the subject is suffering from a thrombotic disorder.

14. The method of claim 12, wherein the subject is at risk of developing a thrombotic disorder.

15. The method of claim 12, wherein platelet aggregation and/or adhesion in the subject is reduced.

16. The method of claim 12, wherein both platelet aggregation and platelet adhesion in the subject are reduced.

17. The method of claim 12, wherein the thrombotic disorder is selected from stroke, myocardial infarction, unstable angina, abrupt closure following angioplasty or stent placement, thrombosis induced by peripheral vascular surgery, peripheral vascular disease and thrombotic disorders resulting from atrial fibrillation or inflammation.

18. The method of claim 12, further comprising administering to the subject an effective amount of at least one therapeutic agent selected from the group consisting of anti-coagulant agents, antiplatelet agents, and fibrinolytic agents.

19. The method of claim 18, wherein the therapeutic agent is selected from the group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, ticagrelor, abciximab, eptifibatide and tirofiban.

20. A method for inhibiting or reducing platelet aggregation and adhesion, comprising administering to a subject in need thereof an effective amount of a compound of claim 1, or a pharmaceutically acceptable salt thereof.

* * * * *